United States Patent [19]

Elfarra

[11] Patent Number: 5,120,740
[45] Date of Patent: Jun. 9, 1992

[54] PRODRUGS OF 6-MERCAPTOPURINE AND 6-THIOGUANINE

[75] Inventor: Adnan A. Elfarra, Madison, Wis.

[73] Assignee: Wisconsin Alumni Research Foundation, Madison, Wis.

[21] Appl. No.: 542,664

[22] Filed: Jun. 25, 1990

Related U.S. Application Data

[63] Continuation-in-part of Ser. No. 432,098, Nov. 3, 1989, abandoned.

[51] Int. Cl.$^5$ .................. A61K 31/495; C07D 473/24; C07D 473/38
[52] U.S. Cl. ................... 514/262; 544/276; 544/265
[58] Field of Search .............. 514/262; 544/276, 265

[56] References Cited

U.S. PATENT DOCUMENTS

| | | | |
|---|---|---|---|
| 2,875,203 | 2/1959 | Shive et al. | 260/252 |
| 2,952,539 | 9/1960 | Dersch et al. | 96/66 |
| 3,149,111 | 9/1964 | Hitchings et al. | 260/252 |
| 3,232,937 | 2/1966 | Hitchings et al. | 260/252 |
| 3,232,938 | 2/1966 | Hitchings et al. | 260/252 |
| 3,238,207 | 3/1966 | Hitchings et al. | 260/252 |
| 3,567,705 | 3/1971 | Cerny et al. | 260/112.5 |
| 4,139,705 | 2/1979 | Dunbar et al. | 544/280 |
| 4,169,948 | 10/1979 | Dunbar et al. | 544/118 |
| 4,443,435 | 4/1984 | Bodor et al. | 424/180 |
| 4,714,701 | 12/1987 | Beauchamp | 544/276 |

FOREIGN PATENT DOCUMENTS

| | | |
|---|---|---|
| 350742 | 1/1990 | European Pat. Off. . |
| 1695744 | 4/1972 | Fed. Rep. of Germany . |
| 3730542 | 4/1989 | Fed. Rep. of Germany . |
| 240663 | 10/1987 | Japan . |

OTHER PUBLICATIONS

Y. Hwang et al., 251, J. Pharm. Exp., 448–454 (1989).
L. Lash et al., 276, Arch. Bio. Biophys., 322–330 (1990).
A. Garcia-Raso et al., 51, J. Org. Chem., 4285–4287 (1986).
M. Winitz et al., 78, J. Amer. Chem. Soc., 2423–2430 (1956).
FASEB Journal, Mar. 20, 1988, Abst. 4922, p. A1143, A. Elfarra et al.
FASEB Journal, Mar. 19, 1989, Abst. 1165, p. A427, A. Elfarra et al.
Vol. 30, Proc. A.A.C.R., Mar. 1989, p. 590, Abstract 2347, R. Robins et al.
Vol. 30, Proc. A.A.C.R., Mar. 1989, p. 596, Abstract 2374, J. Fujitaki et al.
Vol. 30, Proc. A.A.C.R., Mar. 1989, p. 597, R. Finch et al. (Abstract 2375, 2377), R. Willis et al. (Abstract 2376), and G. Crabtree et al. (Abstract 2378).
Vol. 30, Proc. A.A.C.R., Mar. 1989, p. 599, Abstract 2384, T. Riley et al.
K. Van Scoik et al., 16, Drug Metab. Rev., 157–174 (1985).
J. Nelson et al., 46, J. Can. Res., 137–140 (1986).
Raz et al., Pharmacokinetics of Sulfur-35-Labeled N-[-8-(6-purinylthio)valeryl]glycine Ethyl Ester, Advan. Antimicrob. Antineopl. Chemother. Proc. Int. Congress Chemother., 7th, 1971, 2, 59–61.
Hwang, I. Y.; Elfarra, A. A., Cysteine S-Conjugates . . . , J. Pharmacol. Exp. Ther., 1989, vol. 251(2).

Primary Examiner—Mary C. Lee
Assistant Examiner—M. S. H. Gabilan
Attorney, Agent, or Firm—Quarles & Brady

[57] ABSTRACT

Prodrugs for the treatment of kidney tumors are disclosed. The prodrugs are conjugates that can require the cooperation of multiple enzymes in the kidney to release 6-mercaptopurine or 6-thioguanin, or can selectively release 6-thioguanine. Methods for use of these prodrugs are also disclosed.

29 Claims, No Drawings

PRODRUGS OF 6-MERCAPTOPURINE AND 6-THIOGUANINE

This invention was made with U.S. government support awarded by NIH:BRSG. The U.S. government has certain rights in this invention.

This application is a continuation in part of application Ser. No. 07/432,098 filed Nov. 3, 1989, now abandoned.

This invention relates to compounds capable of targeting anti-tumor drugs to the kidney. More specifically, it relates to prodrug conjugates of 6-mercaptopurine and 6-thioguanine that are designed to require exposure to multiple enzymes present in the kidney prior to releasing an anti-tumor agent.

BACKGROUND OF THE INVENTION

The chemical modification of a biologically active drug to give a new chemical from which the active drug can be generated by enzymatic action is an important strategy to target drug action to specific cells and tissues and thereby decrease toxicity or side effects on non-target cells. N. Bodor et al., 22 Ann. Rep. Med. Chem. 303-313 (1987); T. Krenitsky et al., 81 P.N.A.S. USA 3209-3213 (1984); J. Hjelle et al., 229 J. Pharmacol. Exp. Ther. 372-380 (1984); S. Magnan et al., 25 J. Med. Chem. 1018-1021 (1982); M. Orlowski et al., 212 J. Pharmacol. Exp. Ther. 167-172 (1980). The disclosure of these articles and of all other articles listed herein are incorporated by reference as if fully set forth herein. Such compounds are known as "prodrugs".

In A. Elfarra et al. FASEB Journal, Abstract 4922 (Mar. 20, 1988) our laboratory reported that S-(6-purinyl)-L-cysteine, the cysteine derivative of the anti-tumor and immunosuppressant drug 6-mercaptopurine, could be a potential prodrug. In this regard, 6-mercaptopurine is known to be effective in the treatment of various types of tumors. However, it is not actively transported from the G.I. tract, and is readily metabolized by xanthine oxidase to generate biologically inactive metabolites. Thus, it must be given in large doses for a long time to be effective. The concept is that the β-lyase needed to release the 6-mercaptopurine is predominantly found in the kidney. Further, the kidney transport system tends to concentrate amino acid derivatives. This development is of great importance since currently there is no satisfactory chemotherapy technique for treating kidney tumors. While this S-(6-purinyl)-L-cysteine approach had some success, even greater specificity is desired. Further, 6-mercaptopurine may have certain disadvantages for some patients which renders use of 6-thioguanine alternatives desirable.

In separate work, our laboratory has reported that gamma-glutamyl transpeptidase, cysteinyl glycine dipeptidase, and cysteine conjugate β-lyase are all present in the kidney and may cooperatively act to release an S-(1,2-dichlorovinyl) thio moiety from S-(1,2-dichlorovinyl glutathione). A. Elfarra et al., 35 Biochem. Pharm. 283-288 (1986). Also, it has been reported that the renal acylase and the renal esterase are prevalent in the kidney.

It has also been reported in A. Elfarra et al., 83 P.N.A.S. U.S.A. 2667, 2670 (1986) that a homocysteine S-conjugate of dichlorovinyl could undergo transamination in the kidney to yield the corresponding 2-keto acid, and that non-enzymatic elimination under the conditions present in the kidney would then release the dichlorovinyl group. The S-conjugate of the hydroxy analogue is also toxic as it is metabolized to the keto-acid in the kidney by amino acid oxidases. See L. Lash et al. 276 Arch. Biochem. Biophys. 322 (1990).

Thus, it can be seen that a need exists for the development of more specific kidney prodrugs.

SUMMARY OF THE INVENTION

One embodiment of the present invention provides a compound having the formula:

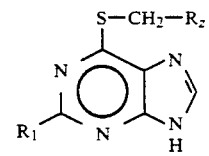

where $R_1$ is selected from the group consisting of H and $NH_2$; and where $R_2$ is selected from the group consisting of:

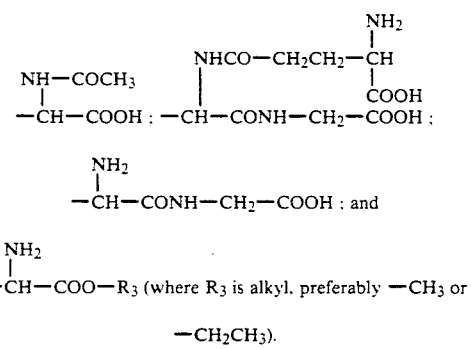

$$-CH-COO-R_3 \text{ (where } R_3 \text{ is alkyl, preferably } -CH_3 \text{ or } -CH_2CH_3\text{)}.$$

In another aspect, the invention provides a compound having the formula:

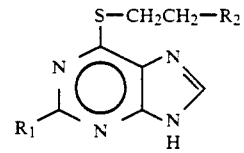

where $R_1$ is selected from the group consisting of H and $NH_2$; and where $R_2$ is selected from the group consisting of:

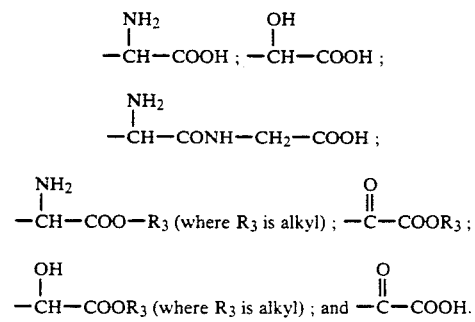

In another aspect, the invention provides methods of inhibiting tumor development in a mammalian kidney involving exposing the kidney to one or more of these compounds.

Most of the above prodrugs require multiple enzyme activity prior to releasing 6-mercaptopurine or thioguanine. In this regard, the glutathione variants require action by gamma-glutamyl transpeptidase (which releases a glutamate moiety), cysteinyl qlycine dipeptidase (which releases a glycine residue), and cysteine conjugate β-lyase. The cysteinyl glycine variants require use of the latter two enzymes to release the antitumor agent. The acetyl variants require use of renal acylase and then β-lyase. The ester variants require use of renal esterase and renal β-lyase.

Because these five enzymes are predominantly found in the kidney, because of the kidney's ability to concentrate amino acid derivatives, and because significant concentrations of the combination of these five enzymes are not found in many other parts of the body, specificity can be achieved through use of these compounds. Similarly, S-conjugates of homocysteine (and of hydroxy analogues thereof) require enzymatic modification to the keto-acid form, followed by further action in the kidney to release the drug.

The objects of the invention therefore include:
(a) providing compounds of the above kind;
(b) providing methods of the above kind for using such compounds to treat mammalian kidney tumors; and
(c) providing methods for synthesizing such compounds.

These and still other objects and advantages of the present invention will be apparent from the description which follows. These embodiments do not represent the full scope of the invention. Rather, the invention may be employed in other embodiments. Reference is therefore made to the claims herein for interpreting the scope of the present invention.

BEST MODES FOR CARRYING OUT THE INVENTION

A detailed synthesis for S-(6-purinyl)-L-cysteine is described below (where $R_1 = H$ and

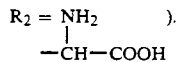

Synthesis of the claimed compounds will then be described with reference to this synthesis. Basically, 6-choroguanine or 6-chloropurine are reacted with the amino acid precursor (glutathione, cysteinyl glycine, N-acetyl-L-cysteine or cysteine alkyl ester, e.g. cysteine methyl ester or cysteine ethyl ester) under the specified conditions to yield the compound of interest. The compounds are then be tested on rat kidney.

Materials

6-Chloropurine, 6-chloroguanine, glutathione, cysteinylglycine, N-acetyl-L-cysteine, 6-mercaptopurine, and 2-chlorobenzothiazole can be obtained from Aldrich Chemical Co. (Milwaukee, WI). Sephadex LH-20 was supplied by Pharmacia Inc. (Piscataway, NJ). L-cysteine, aminooxyacetic acid, cysteine methyl ester, cysteine ethyl ester, and bovine serum albumin can be purchased from Sigma Chemical Co. (St. Louis, MO). As standard for enzyme activity, S-[2-benzylthiazolyl]-L-cysteine ("BTC") was prepared as previously described D. Dohn et al., 120 Anal. Biochem. 379-386 (1982). Supplies for proton NMR were obtained from Wilmad Glass Co. (Buena, NJ). Other cysteinyl alkyl ester starting compounds can be prepared using standard ester formulation reactions. All other reagents were of the highest grade commercially available.

Synthesis Of S-6-Purinyl-L-Cysteine

6-Chloropurine (152 mg; 1.0 mmol) and L-cysteine (182 mg; 1.5 mmol) were dissolved in a mixture of 2.5 mL of 1 N NaOH solution and 2.5 mL of methanol. This lead to the displacement of the chlorine by the disodium salt of cysteine. The reaction mixture was kept under nitrogen and heated in a water bath for 45 minutes at 50° C. with continuous stirring. The reaction mixture was kept in a ice bath until S-6-purinyl-L-cysteine ("PC") was isolated by suing either semi-preparative reverse phase HPLC or by low pressure Sephadex LH-20 chromatography.

For the Sephadex LH-20 chromatography, the reaction mixture (pH 10.2–10.5) was applied to a 2.2×76 cm Sephadex LH-20 column which was kept at 4° C. because of the apparent instability of PC when the Sephadex LH-20 chromatography was carried out at room temperature. Product was separated from the reaction mixture using water, adjusted to pH 10.5 with 1 N NaOH, as eluent. The flow rate was 0.68 mL/minute and 5 minute fractions were collected using a fraction collector. Fractions 55–62 which contained the product were pooled, lyophilized and stored in a desiccator at −20° C. The yield of the compound was approximately 15%.

For the isolation of the compound by semi-preparative HPLC, samples of the reaction mixture (adjusted to pH 5–6 with acetic acid) were applied into a Whatman Partisil 10 ODS 3 magnum-9 HPLC column (9.4 mm×250 mm) attached to a Beckman 114M HPLC pump, a Rheodyne injection valve, a 3 cm long C-18 guard column, a Spectroflow 757 variable wavelength detector (Kratos Analytical Inc., NJ) and a 4270 SP Integrator (Spectra Physics Inc., NJ). The eluent was acetonitrile:water (10:90 % v/v); flow rate was 2.0 mL/minute; detection wavelength was 266 nm. The fractions that contained the product (retention time 11–12 minutes) were collected and kept on ice until it was lyophilized.

Analytical HPLC analyses were done as described for the semi-preparative HPLC except that a 4.6×250 mm Whatman ODS 10 um column was used, and the flow rate was 1 mL/minute.

TLC were developed using 250 um Silicagel GF plates (Analtech Inc., DE) with isopropanol:water:ammonium hydroxide (9:2:1 5 v/v/v). Product was visualized with a UV light (PC had a maximal UV absorption at 284 nm; FIG. 3) or a ninhydrin spray. Rf values of the product, 6-chloropurine, L-cysteine and L-cystine were 0.42, 0.67, 0.05 and 0.2 respectively with the indicated solvent system.

Tests On Kidneys

Male Sprague-Dawley rats (250–350 g) (Charles River Laboratories, Wilmington, MA), were killed by decapitation, and the kidneys were removed. Subcellular fractionation by centrifugation was performed as described by D. Dohn et al., 120 Anal. Biochem. 379–386 (1982). These subcellular fractions were used as the enzyme source without further purification. The protein concentrations of the different fractions were determined according to the procedure of O. Lowry et al., 193 J. Biol. Chem. 265-275 (1951) with bovine serum albumin as the standard.

In a final volume 1.2 mL, each incubation tube contained sodium borate buffer (pH 8.6, 0.1 M); the prodrug (3 mM); and the kidney homogenate (4 mg/mL). Some tubes contained 1 mM aminooxyacetic acid, an inhibitor of β-lyase. Control incubations were carried without the addition of the enzyme. Enzymatic reactions were conducted for 20 minutes at 37° C. in a Dubnoff metabolic incubator with continuous shaking. Reactions were terminated by placing the tubes on ice followed by filteration with 0.2 um Acro LC 13 membrane filters (VWR Scientific Inc., Chicago). HPLC analyses were carried as described earlier with the additional use of an authentic sample of 6-mercaptopurine as a reference.

Renal β-lyase activity was determined with the prodrug as the substrate and the amount of 6-mercaptopurine formed was determined by HPLC. The assay mixture sodium borate buffer (pH 8.6; 0.1 M), and enzyme solution (0.6-1.2 mg/mL). The reaction mixture was incubated at 37° C. for 20 minutes and the reaction was terminated as described above. A portion (20 uL) of the filtrate was injected into the HPLC system. The standard curve obtained by plotting the peak area of the 6-mercaptopurine peak was linear over the range of 1 to 350 uM of 6-mercaptopurine in the incubation mixture.

To determine the effectiveness of the prodrug as a substrate for renal β-lyase, the rates of 6-mercaptopurine production were compared with the rates of metabolism of the prototype β-lyase substrate, BTC (0.5-6 mM in 0.1 M sodium borate buffer, pH 8.6) to form 2-mercaptobenzothiazole (D. Dohn et al., 120 Anal. Biochem. 379-386 (1982)).

My research showed that 6-mercaptopurine is generated by the β-lyase-dependent metabolism of the prodrug. Additional studies showed that 6-mercaptopurine formation was dependent upon incubation time, and substrate- and protein concentrations. The results of the fractionation of various kidneys showed β-lyase activity in different subcellular fractions with the prodrug as the substrate, and show that most of the prodrug dependent β-lyase activity was present in the cytosolic and mitochondrial fractions. These results are in agreement with the subcellular localization of renal β-lyase.

The ability of the kidneys to concentrate amino acid derivatives will result in the accumulation of prodrugs in renal proximal tubular cells where it would be metabolized by β-lyase (and the other required enzymes) to form 6-mercaptopurine or 6-thioguanine. Thus, the kidneys will be exposed to high concentrations of 6-mercaptopurine without exposing other portions of the body to adverse concentrations of such compounds. This has been verified by experiments in vivo on rats.

To synthesize the claimed compounds, one reacts 6-chloropurine or 6-chloroguanine with the precursor thio compound (L-cysteine glutathione, cysteinyl-glycine, cysteine methyl ester, cysteine ethyl ester, other cysteine alkyl ester, or N-acetyl-L-cysteine) under similar conditions to yield S-(6-purinyl)-N-acetyl-L-cysteine; S-(6-purinyl)-cysteinyl-glycine; S-(6-purinyl)-glutathione; S-(6-purinyl)-cysteine methyl ester, S-(6-purinyl)-cysteine ethyl ester, other S-(6-purinyl)-cysteine alkyl esters; S-(6-guanyl)-N-acetyl-L-cysteine; S-(6-guanyl)-cysteinyl-glycine; S-(6-guanyl)-cysteine methyl ester, S-(6-guanyl)-cysteine ethyl ester; other S-(6-guanyl)-cysteine alkyl esters; and S-(6-guanyl)-glutathione. S-(6-guanyl)-L-cysteine can also be formed.

To create the homocysteine variants, one begins by making S-(6-purinyl)-L-homocysteine (Compound H1). To do this, sodium metal is gradually added to a stirred solution of L-homocysteine (Sigma Chemical Co.; 2 mmol) in liquid ammonia (150 ml) until a blue color persisted for ten minutes. The white solid obtained after the evaporation of the ammonia was redissolved in 15 ml water containing EDTA (ethylene diamine tetraacetic acid; Aldrich Chemical co.; 5 mg). 6-Chloropurine (2 mmol; Aldrich Chemical Co.) was added and the pH of the solution was adjusted to 10.8 using a 10% solution of sodium hydroxide (Aldrich Chemical Co.). After refluxing for 2.7 hours, the reaction mixture was cooled to room temperature and the pH was adjusted to 2.7 using a 20% solution of trifluoroacetic acid (Aldrich Chemical Co.). Portions of the reaction mixture (2 ml each) were applied to a Pharmacia KX26 column, and the product was separated using a water (pH 2.5) as eluent. The flow rate was 2.5 ml/min; UV-detection was at 254 nm; Ve was 458 ml. The collects were pooled, lyophilized, and then stored in a desicator.

Synthesis of the thioguanine variant (Compound H2) can be achieved using 6-chloroguanine (Aldrich Chemical Co.) instead of 6-chloropurine. Synthesis of the homocysteine compounds where $R_2$ is

(Compounds H3 and H4 respectively) will be achieved by a modification of the method of M. Winitz et al., 78 J. Amer. Chem. Soc. 2423-2430 (1956). One reacts sodium nitrite (Aldrich Chemical Co.) with Compounds H1 and H2, respectively. The synthesis of related compounds where $R_2$ is

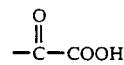

can be achieved by the reaction of Fremy's salt with Compounds H3 and H4, respectively. See generally A. Garcia-Rafo et al. 51 J. Org. Chem. 4285 (1986) (Fremy's salt).

Further Testing

At 30 minutes after treatments of rats (in vivo) with S-purinyl-L-glutathione (0.8 mmol/kg, i.p.), 6-mercaptopurine, and its further metabolites 6-thiouric acid and 6-methylmercaptopurine, were detected in the kidneys at concentrations of nearly 20 nmol metabolites/g wet tissue. These compounds were not detected at all in plasma or liver in this experiment (alneit with some dosages, kill times, and other prodrugs small amounts of 6-mercaptopurine can be detected in the plasma or liver).

At 24 hours after treatments of rats with S-(purinyl)-L-glutathione, S-(purinyl)-N-acetyl-L-cysteine, or S-(purinyl)-L-cysteine ethyl ester (0.4 mmol/kg, i.p.), 6-mercaptopurine and its metabolites were present in urine at levels corresponding to 4, 2, and 1% of the theoretically possible administered dose, respectively.

When rats were given S-(6-purinyl)-homocysteine (0.4 mmol/kg), the amounts of 6-mercaptopurine and the products of its further metabolism which were detected in urine at 24 hour post treatment were at levels corresponding to four times that amount found for S-(6-purinyl)-L-cysteine.

When rats were given the homocysteine variant (0.8 mmol/kg, i.p.) the concentration of metabolites (6-mercaptopurine, 6-methylmercaptopurine, and 6-thiouric acid) present in liver and kidneys at 30 minute post treatment were nearly 10 and 90 nmol/g wet tissue, respectively. No metabolites were detected in plasma. These results show that this compound is a selective kidney precursor of 6-mercaptopurine.

This concept of providing a multiplicity of enzymes to control release 6-mercaptopurine or 6-thioguanine provides a highly advantageous system, and yields prodrugs with improved specificity. Also, thioguanine prodrugs are highly desirable.

It will be appreciated that the above describes only the preferred embodiments of the invention. A number of other modifications and changes are within the scope of the invention and are intended to be included within the scope of the claims. For example, DL (as distinguished from L stereochemistry is included). Also, equivalents such as radio labelled variants are included. Thus, the claims should be looked to in judging the scope of the invention.

I claim:

1. A compound having the formula:

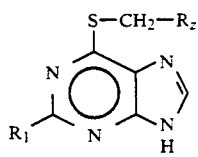

where $R_1$ is selected from the group consisting of H and $NH_2$; and
where $R_2$ is selected from the group consisting of:

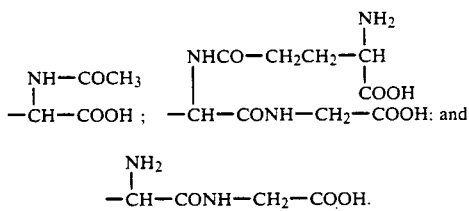

2. The compound of claim 1, wherein $R_1$ is H and $R_2$ is

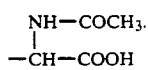

3. The compound of claim 1, wherein $R_1$ is H and $R_2$ is

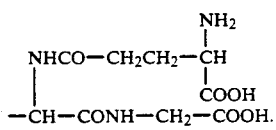

4. The compound of claim 1, wherein $R_1$ is H and $R_2$ is

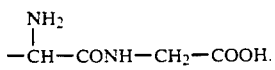

5. The compound of claim 1, wherein $R_1$ is $NH_2$ and $R_2$ is

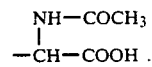

6. The compound of claim 1, wherein $R_1$ is $NH_2$ and $R_2$ is

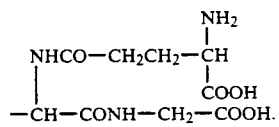

7. The compound of claim 1, wherein $R_1$ is $NH_2$ and $R_2$ is

8. A method of increasing the level of a compound selected from the group of 6-mercaptopurine and 6-thioguanine in a mammalian kidney, comprising the step of exposing the kidney to a compound having the formula:

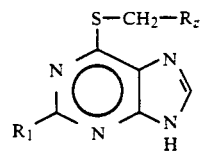

where $R_1$ is selected from the group consisting of H and $NH_2$; and
where $R_2$ is selected from the group consisting of:

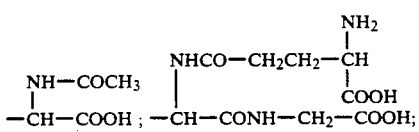

where $R_3$ is alkyl, whereby said level is increased.

9. The method of claim 8 wherein $R_1$ is H and $R_2$ is

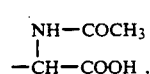

and the level of 6-mercaptopurine is increased.

10. The method of claim 8 wherein $R_1$ is H and $R_2$ is

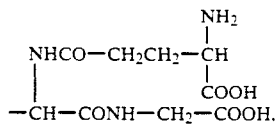

and the level of 6-mercaptopurine is increased.

11. The method of claim 8 where $R_1$ is H and $R_2$ is

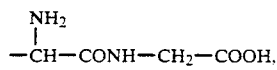

and the level of 6-mercaptopurine is increased.

12. The method of claim 8 where $R_1$ is H and $R_2$ is

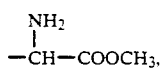

and the level of 6-mercaptopurine is increased.

13. The method of claim 8 where $R_1$ is H and $R_2$ is

and the level of 6-mercaptopurine is increased.

14. The method of claim 8 where $R_1$ is $NH_2$ and $R_2$ is

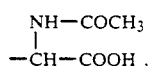

and the level of 6-thioquanine is increased.

15. The method of claim 8 where $R_1$ is $NH_2$ and $R_2$ is

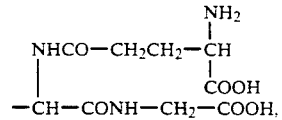

and the level of 6-thioquanine is increased.

16. The method of claim 8 where $R_1$ is $NH_2$ and $R_2$ is

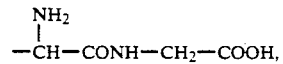

and the level of 6-thioquanine is increased.

17. The method of claim 8 where $R_1$ is $NH_2$ and $R_2$ is

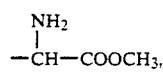

and the level of 6-thioquanine is increased.

18. The method of claim 8 where $R_1$ is $NH_2$ and $R_2$ is

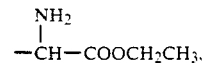

and the level of 6-thioquanine is increased.

19. A method of increasing the level of 6-thioguanine in a mammalian kidney, comprising the step of exposing the kidney to a compound, having the formula:

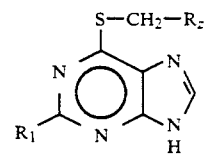

where $R_1$ is $NH_2$; and where $R_2$ is

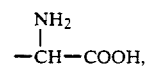

whereby said level is increased.

20. A compound having the formula:

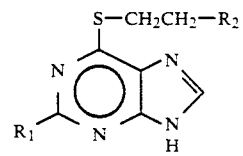

where $R_1$ is selected from the group consisting of H and $NH_2$; and
where $R_2$ is selected from the group consisting of:

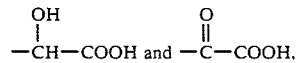

and wherein if $R_1$ is H, then $R_2$ is —CH(OH)—COOH.

21. The compound of claim 20, wherein $R_1$ is H and $R_2$ is

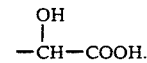

22. The compound of claim 20, wherein $R_1$ is $NH_2$ and $R_2$ is

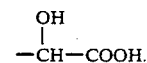

23. The compound of claim 20, wherein $R_1$ is $NH_2$ and $R_2$ is

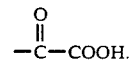

24. A method of increasing the level of 6-mercaptopurine in a mammalian kidney, comprising the step of exposing the kidney to the compound having the formula

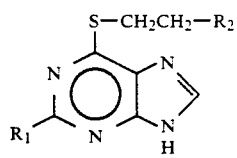

where R₁ is H and R₂ is

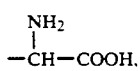

whereby said level is increased.

25. A method of increasing the level of 6-mercaptopurine in a mammalian kidney, comprising the step of exposing the kidney to the compound of claim 21, whereby said level is increased.

26. A method of increasing the level of 6-mercaptopurine in a mammalian kidney, comprising the step of exposing the kidney to the compound having the formula

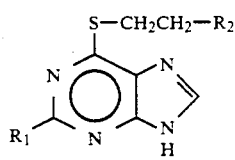

where R1 is H and R2 is

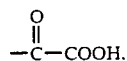

whereby said level is increased.

27. A method of increasing the level of 6-thioguanine in a mammalian kidney, comprising the step of exposing the kidney to the compound having the formula

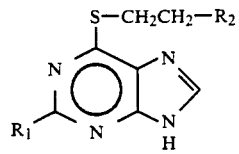

where R₁ is NH₂ and R₂ is

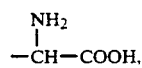

whereby said level is increased.

28. A method of increasing the level of 6-thioguanine in a mammalian kidney, comprising the step of exposing the kidney to the compound of claim 22, whereby said level is increased.

29. A method of increasing the level of 6-thioguanine in a mammalian kidney, comprising the step of exposing the kidney to the compound of claim 23, whereby said level is increased.

* * * * *

UNITED STATES PATENT AND TRADEMARK OFFICE
CERTIFICATE OF CORRECTION

PATENT NO. : 5,120,740
DATED : June 9, 1992
INVENTOR(S) : Adnan A. Elfarra

It is certified that error appears in the above-identified patent and that said Letters Patent is hereby corrected as shown below:

| | |
|---|---|
| Column 3 Line 7 | qlycine  s/b  --glycine-- |
| Column 4 Line 14 | in a ice bath  s/b  --in an ice bath-- |
| Column 4 Line 37 | C-I8  s/b  --C-18-- |
| Column 5 Lines 19-20 | s/b  The assay mixture contained in a final volume of 2mL, prodrug (2-16mM),... |
| Column 6 Line 20 | was separated using a water  s/b  --was separated using water-- |
| Column 6 Line 56 | (alneit s/b  --(albeit-- |
| Claim 14, column 9, line 39 | 6-thioquanine  s/b  --6-thioguanine-- |
| Claim 15, column 9, line 49: | 6-thioquanine  s/b  --6-thioguanine-- |
| Claim 16, column 9, line 58: | 6-thioquanine  s/b  --6-thioguanine-- |
| Claim 17, column 9, line 66: | 6-thioquanine  s/b  --6-thioguanine-- |

UNITED STATES PATENT AND TRADEMARK OFFICE
CERTIFICATE OF CORRECTION

PATENT NO. : 5,120,740

DATED : June 9, 1992

INVENTOR(S) : Adnan A. Elfarra

It is certified that error appears in the above-identified patent and that said Letters Patent is hereby corrected as shown below:

Claim 18, column 10, line 6:  6-thioquanine s/b
--6-thioguanine--

Signed and Sealed this

Seventeenth Day of August, 1993

Attest:

BRUCE LEHMAN

Attesting Officer

Commissioner of Patents and Trademarks